(12) United States Patent
Sommer et al.

(10) Patent No.: US 8,359,784 B2
(45) Date of Patent: Jan. 29, 2013

(54) METHOD FOR CONTROLLING SUBTERRANEAN TERMITE ACTIVITY BY FORMING A BARRIER

(75) Inventors: William T. Sommer, Mendham, NJ (US); Bruce W. Ryser, Tampa, FL (US); James B. Ballard, Medford, NJ (US)

(73) Assignee: FMC Corporation, Philadelphia, PA (US)

( * ) Notice: Subject to any disclaimer, the term of this patent is extended or adjusted under 35 U.S.C. 154(b) by 339 days.

(21) Appl. No.: 12/774,159

(22) Filed: May 5, 2010

(65) Prior Publication Data

US 2010/0287818 A1    Nov. 18, 2010

Related U.S. Application Data

(60) Provisional application No. 61/178,297, filed on May 14, 2009.

(51) Int. Cl.
*A01M 1/20* (2006.01)
*A01M 1/24* (2006.01)
*A01M 17/00* (2006.01)
*A01M 29/00* (2011.01)
*A01M 29/12* (2011.01)

(52) U.S. Cl. .......................... 43/132.1; 43/124; 52/101
(58) Field of Classification Search ................ 43/132.1, 43/124, 131; 52/101
See application file for complete search history.

(56) References Cited

U.S. PATENT DOCUMENTS

| | | | | |
|---|---|---|---|---|
| 1,795,488 A * | 3/1931 | Hill | | 43/124 |
| 1,835,885 A * | 12/1931 | Lipthrott | | 43/131 |
| 2,012,651 A * | 8/1935 | Beall | | 43/124 |
| 2,059,095 A * | 10/1936 | Fellman | | 43/124 |
| 2,087,164 A * | 7/1937 | Purifoy | | 43/124 |
| 2,112,229 A * | 3/1938 | Davis | | 43/124 |
| 2,139,225 A * | 12/1938 | Easling | | 43/131 |
| 2,196,140 A * | 4/1940 | Coffman | | 43/124 |
| 2,451,220 A * | 10/1948 | Hunt | | 43/131 |
| 2,981,025 A * | 4/1961 | Woodson | | 43/124 |
| 3,330,062 A * | 7/1967 | Carter | | 43/124 |
| 3,602,248 A * | 8/1971 | Peacock | | 43/124 |
| 3,676,949 A * | 7/1972 | Ramsey | | 43/124 |
| 3,911,611 A * | 10/1975 | Brinker | | 43/124 |
| 4,040,215 A * | 8/1977 | Totsuka | | 43/132.1 |
| 4,043,073 A * | 8/1977 | Basile | | 43/132.1 |
| 4,625,474 A * | 12/1986 | Peacock et al. | | 43/124 |
| 4,805,341 A * | 2/1989 | Maeda | | 43/132.1 |
| 4,809,462 A * | 3/1989 | Maeda | | 43/132.1 |
| 4,823,520 A * | 4/1989 | Ebeling et al. | | 52/101 |
| 5,094,028 A * | 3/1992 | Hume | | 43/132.1 |
| 5,094,045 A * | 3/1992 | Tamashiro | | 52/101 |
| 5,159,778 A * | 11/1992 | Metzner et al. | | 43/132.1 |
| 5,303,502 A * | 4/1994 | Metzner et al. | | 43/132.1 |
| 5,390,440 A * | 2/1995 | Mihealsick | | 43/124 |
| 5,394,642 A * | 3/1995 | Takaoka | | 43/124 |
| 5,561,941 A * | 10/1996 | Long | | 43/132.1 |
| 5,566,500 A * | 10/1996 | Long | | 43/132.1 |
| 5,819,466 A * | 10/1998 | Aesch et al. | | 43/124 |
| 6,047,498 A * | 4/2000 | Mann | | 43/132.1 |
| 6,205,718 B1 * | 3/2001 | Murphy et al. | | 43/132.1 |
| 6,325,304 B1 * | 12/2001 | Brite et al. | | 43/132.1 |
| 6,397,518 B2 * | 6/2002 | Mann | | 43/132.1 |
| 6,453,628 B2 * | 9/2002 | Traxler | | 43/132.1 |
| 6,463,694 B1 * | 10/2002 | Manciet | | 43/132.1 |
| 6,523,298 B2 * | 2/2003 | Neumann | | 43/132.1 |
| 6,877,272 B2 * | 4/2005 | Hoshall | | 43/132.1 |
| 6,959,516 B2 * | 11/2005 | Williamson et al. | | 52/101 |
| 7,464,499 B1 * | 12/2008 | Jordan | | 43/124 |
| 7,666,254 B1 * | 2/2010 | Amaya et al. | | 106/18.3 |
| 7,726,066 B1 * | 6/2010 | Jordan, Jr. | | 43/132.1 |
| 7,748,160 B1 * | 7/2010 | Jordan, Jr. | | 43/132.1 |
| 7,797,878 B2 * | 9/2010 | Schuster | | 43/130 |
| 2006/0130392 A1 * | 6/2006 | Harrington | | 43/132.1 |
| 2006/0254123 A1 * | 11/2006 | Su | | 43/132.1 |
| 2007/0011958 A1 * | 1/2007 | Nickell et al. | | 52/101 |
| 2007/0074640 A1 * | 4/2007 | Amaya et al. | | 106/160.1 |
| 2008/0282624 A1 * | 11/2008 | Francis et al. | | 52/101 |
| 2009/0000215 A1 * | 1/2009 | Francis et al. | | 52/101 |
| 2010/0107515 A1 * | 5/2010 | Harrington | | 52/101 |
| 2012/0047792 A1 * | 3/2012 | Sala et al. | | 43/131 |
| 2012/0055076 A1 * | 3/2012 | Smith et al. | | 43/131 |

FOREIGN PATENT DOCUMENTS

| | | | |
|---|---|---|---|
| EP | 565250 A1 * | 10/1993 | |
| JP | 59199921 A * | 11/1984 | |
| JP | 61200178 A * | 9/1986 | |
| JP | 07003900 A * | 1/1995 | |
| JP | 10028510 A * | 2/1998 | |
| JP | 2001173117 A * | 6/2001 | |
| JP | 2002294890 A * | 10/2002 | |
| JP | 2003253780 A * | 9/2003 | |
| JP | 2007326843 A * | 12/2007 | |
| JP | 2009040710 A * | 2/2009 | |
| JP | 2009084902 A * | 4/2009 | |
| JP | 2010106541 A * | 5/2010 | |
| JP | 2011117218 A * | 6/2011 | |
| WO | WO 9518532 A1 * | 7/1995 | |

* cited by examiner

*Primary Examiner* — Darren W Ark
(74) *Attorney, Agent, or Firm* — FMC Corporation

(57) ABSTRACT

The present invention is directed to a method of protecting a man made structure containing wood and cellulose materials from subterranean termite damage, including reducing termite tubing on building surfaces, comprising applying a termiticidal composition in a band to the lowest portions of the interior and/or exterior surfaces of the structure, wherein the composition comprises a bifenthrin component.

2 Claims, No Drawings

METHOD FOR CONTROLLING SUBTERRANEAN TERMITE ACTIVITY BY FORMING A BARRIER

FIELD OF THE INVENTION

The present invention relates to methods for protecting a man made structure containing wood and/or other cellulose materials from subterranean termite damage. Particularly, the present invention relates to the application of compositions comprising a bifenthrin component as a barrier between the soil and untreated wood and cellulose materials in the structure.

BACKGROUND OF THE INVENTION

Termites feed upon wood, including structural wood that is either in contact with soil or is in close proximity to soil. Subterranean termites have very little resistance to dehydration and nest in the soil to obtain needed moisture. Subterranean termites build shelter tubes, also known as mud tubes, to travel between the soil and a food source that is nearby but not in direct contact with the soil. These shelter tubes provide a dark, moist environment that protects the termites from sunlight, temperature extremes and attack by predators.

To prevent termite damage termiticides such as permethrin, cypermethrin and bifenthrin, are applied to the soil under and around dwellings as a chemical barrier. For new construction, this is accomplished by applying large amounts of the diluted termiticides to the graded soil before the pouring or construction of the building foundation. For an effective treatment, timing of the treatment is important as not to disturb the barrier formed in the soil. Typically the appropriate application time window is narrow and, in the case of multiple dwelling constructions, the application time does not occur simultaneously. Multiple visits by the applicator may be required in these circumstances as well as the transportation of large quantities of water required to dilute the insecticide/termiticide for application.

For existing buildings, the perimeter of the foundation is trenched and drilled then injected with large quantities of the diluted insecticide/termiticide. Special digging, drilling, mixing and pumping equipment is necessary for treating existing buildings. Applying a perfect barrier is difficult in that gaps or breaks in the barrier due to rain or some other form of physical activity, for example, digging, walking or pipe laying, may disturb the barrier. Termites are able to detect the termite barrier termiticide in the soil and avoid lethal contact. Eventually, foraging termites may locate barrier gaps and gain access into the structure. If these termites find structural wood, they will tunnel back through the barrier gap and recruit other termites into the building.

Another approach to termite control is to apply a termiticide material onto pre-construction wood through spray or spray/vacuum applications. The pyrethroid bifenthrin is used for treating framing timber for use in floor frames, wall frames, roof trusses and subflooring. Although this approach to termite control is effective, it requires the use of expensive application equipment. In addition, timber treated with bifenthrin must be handled very carefully, for example, workers should wear gloves and respirators when cutting, sanding or drilling treated wood. Resealing treatments are required when treated wood is rip sawn, redressed or has the original dimensions significantly altered. Off-cuts, saw dust and general waste from bifenthrin treated wood must not be burned or allowed to enter sewers, drains, dams, or other waterways due to the toxicity of bifenthrin to aquatic organisms thus requiring waste to be placed into containers and disposed of in approved landfills.

Borate compounds have been used in the preventative and/or pretreatment of structures to control subterranean termites. Commercial products that contain borates, for example, BORA-CARE® Termiticide, Insecticide and Fungicide Concentrate available from Nisus Corporation, which contains disodium octaborate tetrahydrate, are toxic to termites only by ingestion. Since termites must ingest the borate compound, a band of at least two feet must be applied in order to ensure that the termites obtain a toxic dose and significant damage to the wooden and cellulose materials in man-made structures can occur before the termites are eradicated. In addition, termites can construct shelter tubes over the borate treatment to reach untreated wood and cellulose containing materials.

Therefore, there exists a need for a safe, inexpensive, easy to use and environmentally friendly way of protecting man-made structures and cellulose materials contained in the structure from subterranean termite damage.

SUMMARY OF THE INVENTION

It has now been found that an entire structure can be protected from termites by applying a relatively narrow band of a termiticidal composition to the lower portion of the structure, generally from ground level of the building to two feet above ground level. The present invention is directed to a method of protecting a man made structure containing wood and cellulose materials from subterranean termite damage wherein a termiticidal composition, comprising the active ingredient bifenthrin, is applied to the lower surfaces of the structure.

DETAILED DESCRIPTION OF THE INVENTION

The present invention is directed to a method of protecting a man made structure containing wood and/or cellulose materials from subterranean termite damage, including reducing termite tubing on building surfaces, comprising applying a termiticidal composition in a band to the lowest portions of the interior and exterior surfaces of the structure, wherein the composition comprises a bifenthrin component. It has now been found that the application of a composition comprising bifenthrin to the lowest interior and exterior building surfaces repels subterranean termites, thereby discouraging termites from forming shelter tubes to reach and feed on untreated wood or cellulose materials contained in the structure. The method of the present invention requires no special equipment or large volumes of water and application can be performed anytime the lower framing of new or old construction is exposed. The method of the present invention is effective in preventing damage from subterranean termites including, but not limited to, Eastern subterranean termites (*Reticulitermes flavipes*) and Formosan subterranean termites (*Coptotermes formosanus*).

The term "bifenthrin" means 2-methylbiphenyl-3-ylmethyl (Z)-(1RS)-cis-3-(2-chloro-3,3,3-trifluoroprop-1-enyl)-2,2-dimethyl cyclopropanecarboxylate.

One aspect of the present invention is directed to treating the lower interior and exterior surfaces of new construction with a termiticidal composition comprising bifenthrin, prior to the installation of insulation, drywall or other interior wall materials, and exterior wall coverings such as siding, brick work, stone or stucco. The composition comprising bifenthrin can be applied using simple equipment such as a paint brush, paint roller, trigger spray bottles, pressurized tank sprayers and the like. A visual indicator dye or colorant, for example FD&C blue dye #1, that is not pesticidal and does not interfere with the activity of bifenthrin can be added to the termiticidal composition containing bifenthrin, for example, to the spray mixture before application in order to provide a visual measure as to the completeness of the application. Preferably the interior and exterior application of the composition comprising bifenthrin is made in a band of from about six inches to about two feet wide from the base of the building, from the building sill plate, or from the lowest point at which subterranean termites could enter a building including crawl space foundation walls; however a band larger than two feet can be applied. The band may be applied to any interior or exterior building material such as, but not limited to, lumber, plywood, logs, wood, wood-form composite products and non-wood building components such as cement, concrete, brick, block, stone, stucco, gypsum, metals, plastics and polymers.

It is preferred that the composition comprising bifenthrin be applied at a rate that is effective in repelling subterranean termites. When diluting the composition comprising bifenthrin with liquid diluents, for example, water, it is preferred that the bifenthrin be present at a use rate of from 0.04% wt/wt to 1.0% wt/wt of bifenthrin to water. More preferred is a rate of application of from 0.04% wt/wt to 0.6% wt/wt of bifenthrin to water. The application of the composition containing bifenthrin is preferably preformed using a spray applicator, applying to run-off.

The termiticidal composition containing bifenthrin may be formulated to contain as little as 0.1%, 0.2% or 0.5% to as much as 95% or more by weight of active ingredient. Useful formulations include: wettable powders, emulsifiable concentrates, flowable formulations, micro-emulsion formulations, suspensions, simple solutions, pressurized sprays, and water-soluble or water miscible granules.

Commercially available formulations of bifenthrin which are suitable for use in the present invention include, but are not limited to: Biflex® Aqua Water Based Termiticide and Insecticide, Bistar® WT Insecticide, Bistar® T&O EC Termiticide, Talstar® P Professional Insecticide, Onyx™ Insecticide and BaseLine™ Pretreat Termiticide, all available from FMC Corporation.

The methods of the present invention are further illustrated by the examples below. The examples serve only to illustrate the invention and should not be interpreted as limiting since further modifications of the disclosed invention will be apparent to those skilled in the art. All such modifications are deemed to be within the scope of the invention as defined in the claims.

EXAMPLE 1

This Example Illustrates One Protocol for a Method of Controlling Subterranean Termite Activity in Wooden Structures Twelve wooden frame structures (4 ft by 3 ft by 4 ft high, four to receive treatment with a bifenthrin solution, four to receive a commercial borate standard treatment and four to be used as untreated controls) were built on one inch thick concrete pads in an area of high subterranean termite pressure, Formosean subterranean termites (Coptotermes formosanus). The structures were constructed using pressure treated sill plates, untreated southern yellow pine studs and untreated plywood walls. A two inch diameter polyethylene pipe was installed in a hole in the center of each concrete pad to simulate a plumbing drain installation, leaving a small gap between the pad and the pipe. A piece of wood was inserted in the gap to encourage local termite pressure. To four of the shed structures, an aqueous mixture containing 0.3% wt/wt of bifenthrin to water (Bistar® WT Insecticide formulation) and FD&C blue dye #1, to provide a visual measure as to the completeness of the application, was sprayed to run-off from ground level to two feet high on the inside walls and studs, on the inside and outside portions of the sill plate, from ground level to two feet high on the outside walls and about one foot in diameter onto the concrete surrounding the polyethylene pipe using a compressed air sprayer. Four of the shed structures were sprayed as described above with an aqueous solution of a commercially available borate (BORA-CARE® Termiticide, Insecticide and Fungicide Concentrate prepared as directed by the label as a 1:1 mixture with water) mixed with FD&C blue dye #1. A roof was placed on each structure to protect the inside surfaces from the weather. Four of the shed structures were left untreated. Termite activity surrounding each structure was monitored by installing commercially available in-ground termite monitors (FIRSTLINE® Defender kits available from FMC Corporation) about one foot from each outside face, a total of four monitors per structure. The in-ground monitors were refilled with a new wood inserts as needed. Termite activity was measured in each structure by visually inspecting the inside and outside walls and the area around the polyethylene pipe for termite damage and for construction of shelter tubes at for up to 18 months after treatment. The bifenthrin treated structures received very little or no damage due to termite activity while several of the untreated structures and structures treated the borate standard had evidence of termite destruction. None of the bifenthrin treated structures had any indication of termite damage or damage to the wood piece inserted in the simulated plumbing drain hole. Table 1 below summarizes the data collected during the test period.

TABLE 1

Subterranean Termite Activity On Bifenthrin Treated and Untreated Wooden Structures

| Shed number | Treatment | Live Termites Present | New Shelter Tubes Constructed After last Inspection | In-ground Monitor Stations Exhibiting Termite Activity |
|---|---|---|---|---|
| 60 Days After Treatment ||||||
| 1 | Borate | Yes | 2 | 2 |
| 2 | Borate | Yes | 10 | 2 |
| 3 | Borate | Yes | 1 | 1 |
| 4 | Borate | Yes | 1 | 0 |
| 5 | Bifenthrin | No | 0 | 1 |
| 6 | Bifenthrin | No | 0 | 1 |
| 7 | Bifenthrin | No | 0 | 1 |
| 8 | Bifenthrin | No | 0 | 2 |
| 9 | Untreated | Yes | 3 | 1 |
| 10 | Untreated | No | 2 | 1 |
| 11 | Untreated | No | 0 | 0 |
| 12 | Untreated | No | 0 | 1 |
| 113 Days After Treatment ||||||
| 1 | Borate | Yes | 8 | 4 |
| 2 | Borate | Yes | 6 | 3 |
| 3 | Borate | Yes | 1 | 4 |
| 4 | Borate | Yes | 2 | 2 |
| 5 | Bifenthrin | No | 0 | 4 |
| 6 | Bifenthrin | No | 1* | 3 |
| 7 | Bifenthrin | No | 0 | 1 |
| 8 | Bifenthrin | No | 0 | 1 |
| 9 | Untreated | Yes | 4 | 1 |
| 10 | Untreated | Yes | 3 | 3 |
| 11 | Untreated | No | 0 | 1 |
| 12 | Untreated | No | 0 | 2 |

TABLE 1-continued

Subterranean Termite Activity On Bifenthrin Treated and Untreated Wooden Structures

| Shed number | Treatment | Live Termites Present | New Shelter Tubes Constructed After last Inspection | In-ground Monitor Stations Exhibiting Termite Activity |
|---|---|---|---|---|
| 196 Days After Treatment | | | | |
| 1 | Borate | Yes | 2 | No Data |
| 2 | Borate | Yes | 6 | No Data |
| 3 | Borate | Yes | 1 | No Data |
| 4 | Borate | Yes | 1 | No Data |
| 5 | Bifenthrin | No | 0 | No Data |
| 6 | Bifenthrin | No | 0 | No Data |
| 7 | Bifenthrin | No | 0 | No Data |
| 8 | Bifenthrin | No | 0 | No Data |
| 9 | Untreated | No | 4 | No Data |
| 10 | Untreated | Yes | 1 | No Data |
| 11 | Untreated | No | 0 | No Data |
| 12 | Untreated | No | 0 | No Data |
| 250 Days After Treatment | | | | |
| 1 | Borate | Yes | 3 | No Data |
| 2 | Borate | Yes | 7 | No Data |
| 3 | Borate | Yes | 1 | No Data |
| 4 | Borate | Yes | 2 | No Data |
| 5 | Bifenthrin | No | 0 | 4 |
| 6 | Bifenthrin | No | 0 | 3 |
| 7 | Bifenthrin | No | 0 | 0 |
| 8 | Bifenthrin | No | 0 | 2 |
| 9 | Untreated | Yes | 2 | 1 |
| 10 | Untreated | Yes | 2 | 3 |
| 11 | Untreated | No | 0 | 0 |
| 12 | Untreated | No | 0 | 0 |
| 12 Months After Treatment | | | | |
| 1 | Borate | Yes | 4 | No Data |
| 2 | Borate | Yes | 2 | No Data |
| 3 | Borate | Yes | 1 | No Data |
| 4 | Borate | No | 0 | No Data |
| 5 | Bifenthrin | No | 0 | No Data |
| 6 | Bifenthrin | No | 0 | No Data |
| 7 | Bifenthrin | No | 0 | No Data |
| 8 | Bifenthrin | No | 0 | No Data |
| 9 | Untreated | No | 0 | No Data |
| 10 | Untreated | Yes | 2 | No Data |
| 11 | Untreated | No | 0 | No Data |
| 12 | Untreated | No | 0 | No Data |
| 14 Months After Treatment | | | | |
| 1 | Borate | Yes | 2 | No Data |
| 2 | Borate | Yes | 6 | No Data |
| 3 | Borate | Yes | 1 | No Data |
| 4 | Borate | No | 0 | No Data |
| 5 | Bifenthrin | No | 0 | No Data |
| 6 | Bifenthrin | No | 0 | No Data |
| 7 | Bifenthrin | No | 0 | No Data |
| 8 | Bifenthrin | No | 0 | No Data |
| 9 | Untreated | No | 0 | No Data |
| 10 | Untreated | No | 0 | No Data |
| 11 | Untreated | No | 0 | No Data |
| 12 | Untreated | No | 0 | No Data |
| 16 Months After Treatment | | | | |
| 1 | Borate | No | 0 | No Data |
| 2 | Borate | No | 0 | No Data |
| 3 | Borate | No | 0 | No Data |
| 4 | Borate | No | 0 | No Data |
| 5 | Bifenthrin | No | 0 | No Data |
| 6 | Bifenthrin | No | 0 | No Data |
| 7 | Bifenthrin | No | 0 | No Data |
| 8 | Bifenthrin | No | 0 | No Data |
| 9 | Untreated | No | 0 | No Data |
| 10 | Untreated | No | 0 | No Data |
| 11 | Untreated | No | 0 | No Data |
| 12 | Untreated | No | 0 | No Data |
| 18 Months After Treatment | | | | |
| 1 | Borate | Yes[1] | 3 | 1 |
| 2 | Borate | Yes[1] | 1 | 0 |
| 3 | Borate | Yes[1] | 1 | 2 |
| 4 | Borate | Yes[1] | 1 | 2 |
| 5 | Bifenthrin | No | 0 | 1 |
| 6 | Bifenthrin | No | 1** | 0 |
| 7 | Bifenthrin | No | 0 | 2 |
| 8 | Bifenthrin | No | 0 | 3 |
| 9 | Untreated | No | 0 | 0 |
| 10 | Untreated | Yes | 2 | 1 |
| 11 | Untreated | No | 0 | 0 |
| 12 | Untreated | No | 0 | 1 |

*A one inch shelter tube was formed and abandoned by termites. No live termites found in or on the shed.
**A shelter tube was formed over the treated area, to the top of the shed and along the roof line and was abandoned by the termites. A $1/8^{th}$ inch scouring to the wood surface on one vertical stud was observed.
[1]Termite damage to studs is significant with up to 50% damage to some studs.

As can be seen from the data presented in Table 1, applying a bifenthrin solution along the base, inside and outside, of wooden structures is an effective method of discouraging Formosan subterranean termites from building shelter tubes and preventing termite destruction of wooden structures.

EXAMPLE 2

This Example Illustrates One Protocol for a Method of Controlling Subterranean Termite Activity on Exposed Wood Wooden units (Tee-Joints) were constructed for termite testing as follows: a two foot length of 2×4 lumber was fastened, at a right angle by toe-nailing, to the center of a three foot length of 2×4 lumber, the two foot piece of lumber simulating a wall stud and the three foot length simulating a building sill plate. The lumber used for the wall studs was selected from Green Douglas Fir (GDF), Spruce Pine Fir (SPF) or Hemlock Fir-Kiln Dried (HF-KD). The sill plate wood was selected from Green Douglas Fir (GDF), Spruce Pine Fir (SPF), Kiln Dried Hemlock Fir (HF-KD) or Pressure Treated Southern Yellow Pine (PT-SYP).

Four of the Tee-Joint units were used as untreated controls and were constructed solely of SPF lumber. A micro-emulsion of bifenthrin consisting of 8.32% technical bifenthrin (96.2% purity), 85.6% surfactants, 6.06% water and 0.02% of a 50% solution of FD&C blue dye #1, wherein all %'s are % by weight, or ONYX™ Insecticide containing FD&C blue dye #1 was diluted with water to provide test solutions containing either 0.04% by weight or 0.4% by weight of bifenthrin. The remaining Tee-Joint units, constructed of different combinations of lumber, were sprayed to run off with aqueous test solutions containing either 0.04% by weight or 0.4% by weight bifenthrin using a compressed air sprayer. Commercially available termite monitoring stations (FIRST-LINE® Defender kits available from FMC Corporation) were installed in a field actively infested with Eastern subterranean termites (*Reticulitermes flavipes*). A standard size clay building brick was placed on top of each monitoring station and a treated or untreated Tee-Joint unit was placed on top of the brick to avoid direct ground contact. To encourage termite infestation a piece of corrugated cardboard was affixed to each side of the Tee-Joint, extending from the top of the termite monitor up to the butt joint of the wall stud to the sill plate. After 15 months, the treated and untreated Tee-Joints were visually inspected for termite activity, such as shelter tube formation and visible termite destruction. Table 2 below summarizes the data collected after 15 months.

TABLE 2

Control Of Subterranean Termite Activity On Exposed Wood

| Stud Lumber | Sill Lumber | *Bifenthrin Formulation | Concentration of active in Spray % by Weight | Comments |
|---|---|---|---|---|
| SPF | SPF | Untreated Control | N/A | Shelter tube formed to stud/sill joint. Termite damage on both sides of stud. Some termite destruction visible on sill plate. |
| SPF | SPF | Untreated Control | N/A | Shelter tube formed to bottom of stud. No visible termite destruction. |
| SPF | SPF | Untreated Control | N/A | Shelter tube formed to stud/sill joint and around bottom of stud. No visible termite destruction |
| SPF | SPF | Untreated Control | N/A | Shelter tube formed to 1.5 feet high on one side of stud. No visible termite destruction. |
| HF-KD | HF-KD | A | 0.04% | No shelter tubes, no termite destruction. |
| HF-KD | HF-KD | A | 0.04% | No shelter tubes, no termite destruction. |
| SPF | SPF | A | 0.04% | No shelter tubes, no termite destruction. |
| SPF | SPF | A | 0.04% | No shelter tubes, no termite destruction. |
| GDF | PT-SYP | A | 0.04% | No shelter tubes, no termite destruction. |
| GDF | PT-SYP | A | 0.04% | No shelter tubes, no termite destruction. |
| SPF | PT-SYP | A | 0.04% | No shelter tubes, no termite destruction. |
| SPF | PT-SYP | A | 0.04% | No shelter tubes, no termite destruction. |
| GDF | GDF | A | 0.04% | No shelter tubes, no termite destruction. |
| GDF | GDF | A | 0.04% | No shelter tubes, no termite destruction. |
| HF-KD | HF-KD | A | 0.04% | No shelter tubes, no termite destruction. |
| HF-KD | HF-KD | A | 0.04% | No shelter tubes, no termite destruction. |
| SPF | SPF | A | 0.4% | No shelter tubes, no termite destruction. |
| SPF | SPF | A | 0.4% | No shelter tubes, no termite destruction. |
| SPF | SPF | A | 0.4% | No shelter tubes, no termite destruction. |
| SPF | SPF | A | 0.4% | No shelter tubes, no termite destruction. |
| SPF | SPF | B | 0.4% | No shelter tubes, no termite destruction. |
| SPF | SPF | B | 0.4% | No shelter tubes, no termite destruction. |
| GDF | PT-SYP | B | 0.4% | No shelter tubes, no termite destruction. |
| GDF | PT-SYP | B | 0.4% | No shelter tubes, no termite destruction. |
| SPF | PT-SYP | B | 0.4% | No shelter tubes, no termite destruction. |
| SPF | PT-SYP | B | 0.4% | No shelter tubes, no termite destruction. |
| GDF | GDF | B | 0.4% | No shelter tubes, no termite destruction. |
| GDF | GDF | B | 0.4% | No shelter tubes, no termite destruction. |

*A is a micro-emulsion formulation of bifenthrin; B is Onyx ™ Insecticide.

As can be seen from the data in Table 2, spraying sill plate and stud lumber with a bifenthrin solution is an effective method for the prevention of termite shelter tube formation and termite wood destruction.

While this invention has been described with an emphasis upon preferred embodiments, it will be understood by those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of protecting a man-made structure containing wood and cellulose materials from subterranean termite damage comprising applying a termiticidal composition in a band to the structure or unassembled elements of the structure, the termiticidal composition comprising a bifenthrin component present at a use rate of from 0.04% wt/wt to 0.6% wt/wt of bifenthrin to water and a visual indicator dye, the termitcidal composition applied by spraying, brushing or rolling to interior and/or exterior surfaces of the structure or unassembled elements of the structure closest to which subterranean termites could access the structure, the resulting band at least six inches in width and essentially continuous.

2. The method of claim 1 wherein said band is at least two feet in width.

* * * * *